United States Patent
Lin et al.

(10) Patent No.: US 10,111,814 B2
(45) Date of Patent: Oct. 30, 2018

(54) DESENSITIZING TOOTHPASTE

(71) Applicant: National Taipei University of Technology, Taipei (TW)

(72) Inventors: Feng-Huei Lin, Guishan Township, Taoyuan County (TW); Chun-Pin Lin, Taipei (TW); Chia-Ming Chang, Taichung (TW); Tzu-Piao Tang, Taipei (TW); Chung-King Hsu, Taipei (TW); Hsu-Wei Fang, Taipei (TW); Hsuan-Yu Chen, Taichung (TW)

(73) Assignee: NATIONAL TAIPEI UNIVERSITY OF TECHNOLOGY, Taipei, Taiwan (CN)

(*) Notice: Subject to any disclaimer, the term of this patent is extended or adjusted under 35 U.S.C. 154(b) by 0 days.

(21) Appl. No.: 13/922,976

(22) Filed: Jun. 20, 2013

(65) Prior Publication Data
US 2014/0314694 A1 Oct. 23, 2014

(30) Foreign Application Priority Data
Apr. 19, 2013 (TW) .............. 102207239 U

(51) Int. Cl.
| | | |
|---|---|---|
| *A61Q 11/00* | (2006.01) | |
| *A61K 8/24* | (2006.01) | |
| *A61K 8/25* | (2006.01) | |
| *A61K 33/08* | (2006.01) | |
| *A61K 33/42* | (2006.01) | |
| *A61K 8/55* | (2006.01) | |
| *A61K 6/00* | (2006.01) | |
| *A61K 8/19* | (2006.01) | |

(52) U.S. Cl.
CPC ............. *A61K 8/25* (2013.01); *A61K 8/19* (2013.01); *A61K 8/24* (2013.01); *A61Q 11/00* (2013.01)

(58) Field of Classification Search
CPC ........ A61Q 11/00; A61K 8/24; A61K 33/42; A61K 8/25; A61K 33/08; A61K 33/06; A61K 8/55
See application file for complete search history.

(56) References Cited

U.S. PATENT DOCUMENTS

| | | | | |
|---|---|---|---|---|
| 5,215,740 | A | * | 6/1993 | Domke et al. ............ 424/52 |
| 5,891,233 | A | * | 4/1999 | Salonen ............ A61K 6/0276 |
| | | | | 106/35 |
| 2003/0152525 | A1 | * | 8/2003 | Dixon et al. ............ 424/50 |
| 2004/0057908 | A1 | * | 3/2004 | Bowen et al. ............ 424/49 |
| 2005/0142077 | A1 | * | 6/2005 | Zimmer et al. ............ 424/57 |

OTHER PUBLICATIONS

Lee et al. In vitro study of DP-bioglass paste for treatment of dentin hypersensitivity. Sep. 14, 2005. Dental Materials Journal. vol. 24. Issue 4. pp. 562-569.*
Sitharaman, Balaji. Nanobiomaterials Handbook. (2011). CRC Press—Taylor & Francis Group. p. 3-7.*
"Principles of Designing Glass-Ceramic Formation," by Wolfram Holand and George H. Beall, Glass-Ceramic Technology, 2nd edition (2012), pp. 1-2.
"Tribological Properties of Hot Pressed Alumina-Silicon Carbide Nanocomposite," by Seung-Ho Kim, Yoon-Ho Kim, Tohru Sekino, Keichi Niihara and Soo W. Lee, the AZo Journal of Materials Online (Sep. 2005), pp. 1-12.
"Mechanical properties of a new type of apatite-containing glass-ceramic for prosthetic application," by Tadashi Kokubo, Setsuro Ito, Masazumi Shigematsu and Sumio Sakka, Journal of Materials Science 20 (1985), pp. 2001-2004.
"Crystallization Kinematics and Dielectric Behavior of (Ba,Sr)TiOsub3 Borosilicate Glass Ceramics," by Avadhesh Kumar Yadav, Chandkiram Gautam and Prabhakar Singh, New Journal of Glass and Ceramics (2012), pp. 126-131.

* cited by examiner

*Primary Examiner* — Tracy Liu
(74) *Attorney, Agent, or Firm* — Juan Carlos A. Marquez; Marquez IP Law Office, PLLC

(57) ABSTRACT

The present invention discloses a desensitizing toothpaste. Based on the total weight of the desensitizing toothpaste, the desensitizing toothpaste includes: from 5% to 40% by weight of DP-bioglass; from 1% to 5% by weight of thickening agents; from 25% to 35% by weight of humectant; and from 1% to 5% by weight of surfactant, wherein the DP-bioglass includes: 8.4% of $Na_2O$, 40.6% of CaO, 39% of $SiO_2$, and 12% of $P_2O_5$ based on the total weight of the DP-bioglass. With the implementation of the present invention, the indication of dentin hypersensitivity can be greatly relieved.

5 Claims, 10 Drawing Sheets

DESENSITIZING TOOTHPASTE

BACKGROUND OF THE INVENTION

1. Technical Field

The present invention relates to desensitizing toothpastes, and more particularly, to a desensitizing toothpaste that contains DP-bioglass.

2. Description of Related Art

Dentin hypersensitivity, one of common dental diseases, has a prevalence rate of about 8% to 35%. However, therapy that offers instant and lasting cure is seldom available to patients diagnosed with dentin hypersensitivity. As a result, dentin hypersensitivity is an important topic in dentistry.

FIG. 1 shows a cross-sectional view of a conventional tooth and an enlarged view of part of the surface of the tooth. As shown in FIG. 1, the tooth consists of enamel 10, dentin 20, and pulp 30, which are arranged in an inward order. Dentin 20 essentially includes hydroxyapatite and has plenty dentinal tubules 21 which connect enamel 10 and pulp 30. Pulp 30 has therein nerve 31, blood vessels, and lymphatic vessels.

The typical cause of dentin hypersensitivity is as follows: due to abrasion or erosion of enamel 10, dentin 20 is exposed to thereby allow dentinal fluid within the dentinal tubules 21 to flow inward or outward in response to a change of temperature or pH value in the oral cavity; hence, the flow of dentinal fluid indirectly activates the nerve 31 to produce a sense of pain. Therefore, after beginning to drink cold water or eat, patients with dentin hypersensitivity are likely to perceive pain, because the nerve 31 in the pulp 30 is activated.

Conventional methods of medical treatment for dentin hypersensitivity are as follows: 1. protein precipitation: a related procedure is performed to allow the fluid in the dentinal tubules to undergo protein precipitation and flow less, thereby reducing the chance of activation of nerve, but this method has a drawback, that is, the cure thus achieved does not last long; 2. inhibition of nerve activation: nerve conduction is blocked with potassium ions to thereby alleviate pain, but this method has a drawback, that is, the pain is alleviated rather than prevented; and 3. dentinal tubule occlusion: the dentinal tubules are occluded with chemicals to reduce the diameter of the dentinal tubules and close the dentinal tubules, thereby shutting out external stimuli. The aforesaid methods, coupled with simple convenient use applications, such as tooth brushing, mouth rinsing, and painting, are effective in alleviating dentin hypersensitivity. Out of the above options, toothpaste is most convenient to use and most cost-effective.

FIG. 2 shows an SEM micrograph taken of a dentin specimen after use of a conventional desensitizing toothpaste. As shown in FIG. 2, after the use of a commercially-available dentinal tubule occlusion-based desensitizing toothpaste, crystalline substances do not deposit in the dentinal tubules, and the openings of the dentinal tubules are not effectively occluded; as a result, dentin hypersensitivity remains unabated. Hence, it is imperative to provide a desensitizing toothpaste effective in effectuating deposition in the dentinal tubules and occlusion of the dentinal tubules.

SUMMARY OF THE INVENTION

The present invention provides a desensitizing toothpaste, including DP-bioglass, a thickening agent, a humectant, and a surfactant. Based on the total weight of the DP-bioglass, the DP-bioglass contains 8.4% of $Na_2O$, 40.6% of CaO, 39% of $SiO_2$, and 12% of $P_2O_5$. The objective of the present invention is to achieve lasting alleviation of dentin hypersensitivity by dentinal tubule occlusion.

The present invention provides a desensitizing toothpaste, comprising: DP-bioglass comprising 8.4% of $Na_2O$, 40.6% of CaO, 39% of $SiO_2$, and 12% of $P_2O_5$ based on total weight of the DP-bioglass, wherein the desensitizing toothpaste comprises 5% to 40% by weight of the DP-bioglass based on total weight of the desensitizing toothpaste; a thickening agent which accounts for 1% to 5% of the total weight of the desensitizing toothpaste; a humectant which accounts for 25% to 35% of the total weight of the desensitizing toothpaste; and a surfactant which accounts for 1% to 5% of the total weight of the desensitizing toothpaste.

Implementation of the present invention at least involves the following inventive steps:

1. occlude dentinal tubules in a simple and efficient manner; and
2. alleviate dentin hypersensitivity in the long term.

The detailed features and advantages of the present invention will be described in detail with reference to the preferred embodiment so as to enable persons skilled in the art to gain insight into the technical disclosure of the present invention, implement the present invention accordingly, and readily understand the objectives and advantages of the present invention by perusal of the contents disclosed in the specification, the claims, and the accompanying drawings.

DETAILED DESCRIPTION OF THE INVENTION

In an embodiment of the present invention, a desensitizing toothpaste includes DP-bioglass, a thickening agent, a humectant, and a surfactant.

Based on its total weight, the DP-bioglass includes 8.4% of $Na_2O$, 40.6% of CaO, 39% of $SiO_2$, and 12% of $P_2O_5$. The DP-bioglass manifests high biocompatibility and serves as a bone graft material which can be firmly bonded to bone surface. Furthermore, the DP-bioglass has high calcium and phosphorus content but low $SiO_2$ content; hence, the DP-bioglass not only has high solubility, but also releases a large amount of calcium ions and phosphate ions instantaneously as soon as it dissolves. When applied to the manufacturing of a desensitizing toothpaste, the DP-bioglass dissolves instantaneously soon after tooth brushing has begun, and increases the concentration of calcium ions and phosphate ions in the oral cavity instantaneously. Once the concentration of the calcium ions and the phosphate ions exceeds solubility product constant (ksp), the calcium ions and the phosphate ions which pervade dentinal tubules as a result of the dissolution of the DP-bioglass will precipitate to form hydroxyapatite crystalline to occlude the dentinal tubules, thereby achieving lasting alleviation of dentin hypersensitivity.

The DP-bioglass is manufactured in a way described as follows: raw materials $Na_2O$, CaO, $SiO_2$, and $P_2O_5$ provided in percentage by weight 8.4%, 40.6%, 39%, and 12%, respectively, are mixed and then put in a mill pot; afterward, 10 alumina balls each with a diameter of 1 cm, 10 alumina balls each with a diameter of 0.5 cm, and 10 alumina balls each with a diameter of 0.3 cm are put in the mill pot to serve as a mixing medium; then, add 100 ml of ethanol to enable wet grinding; perform ball milling for 8 hours, and then remove the alumina balls; afterward, put the raw materials in an oven operating at 80° C. to evaporate the ethanol, so as to obtain batch material powder which has been evenly mixed; pour the batch material powder into a platinum crucible, and heat the batch material powder in a high-temperature furnace at 1410° C. for 1.5 hours to synthesize glass; as soon as the glass melts, take the molten glass out of the high-temperature furnace, and pour the molten glass quickly into a stainless steel reactor filled with water so as to quench the molten glass; afterward, the glass which has undergone quench cracking is put in the 80° C. oven and dried therein; then, the dried glass is ground to powder with a grinder, and then the powder particles are sieved through a 400-mesh sieve to finalize the manufacturing of the DP-bioglass powder.

Figure 1:
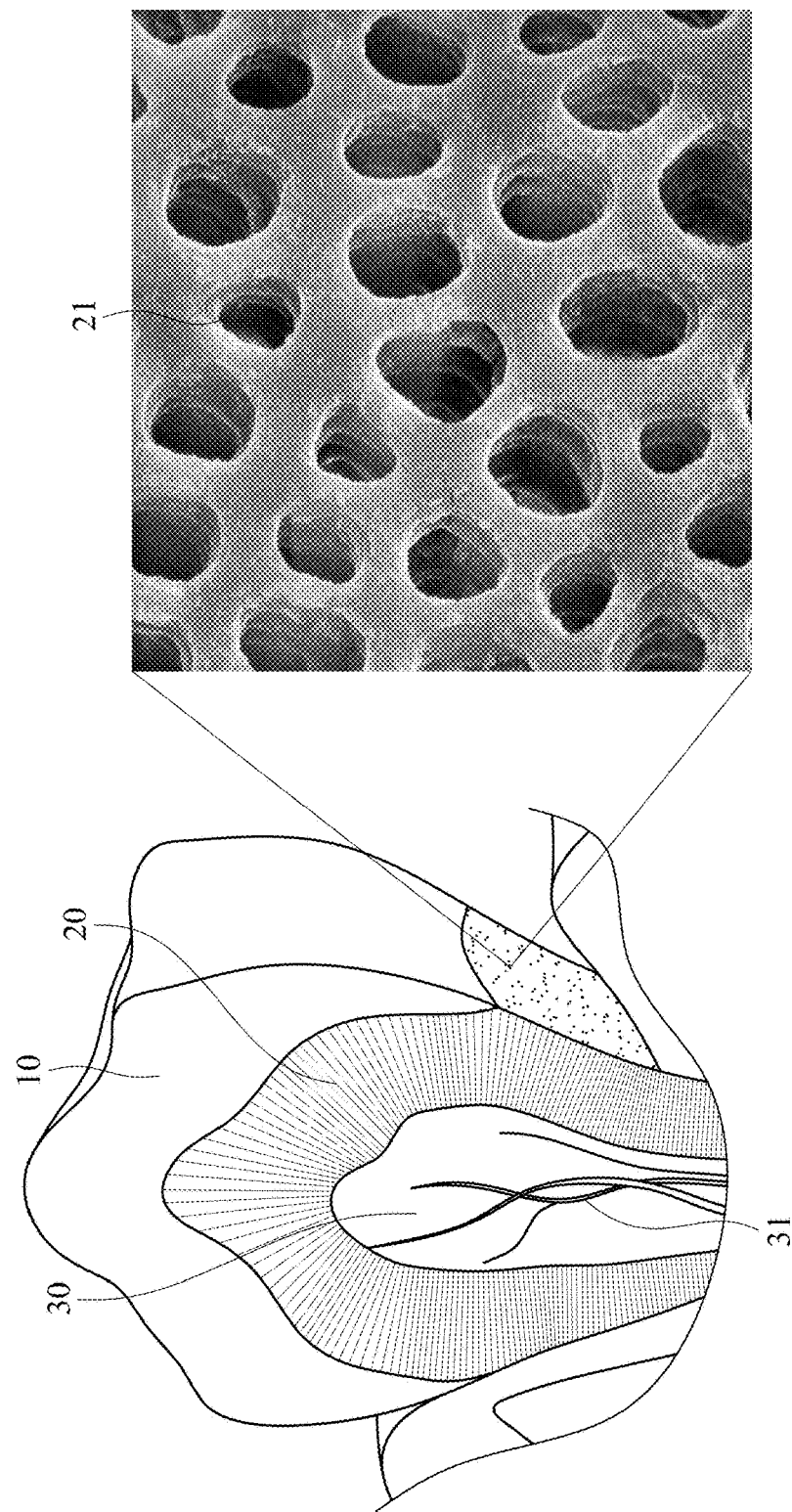
FIG. 1 shows a cross-sectional view of a conventional tooth and an enlarged view of part of the surface of the tooth.
Figure 2:
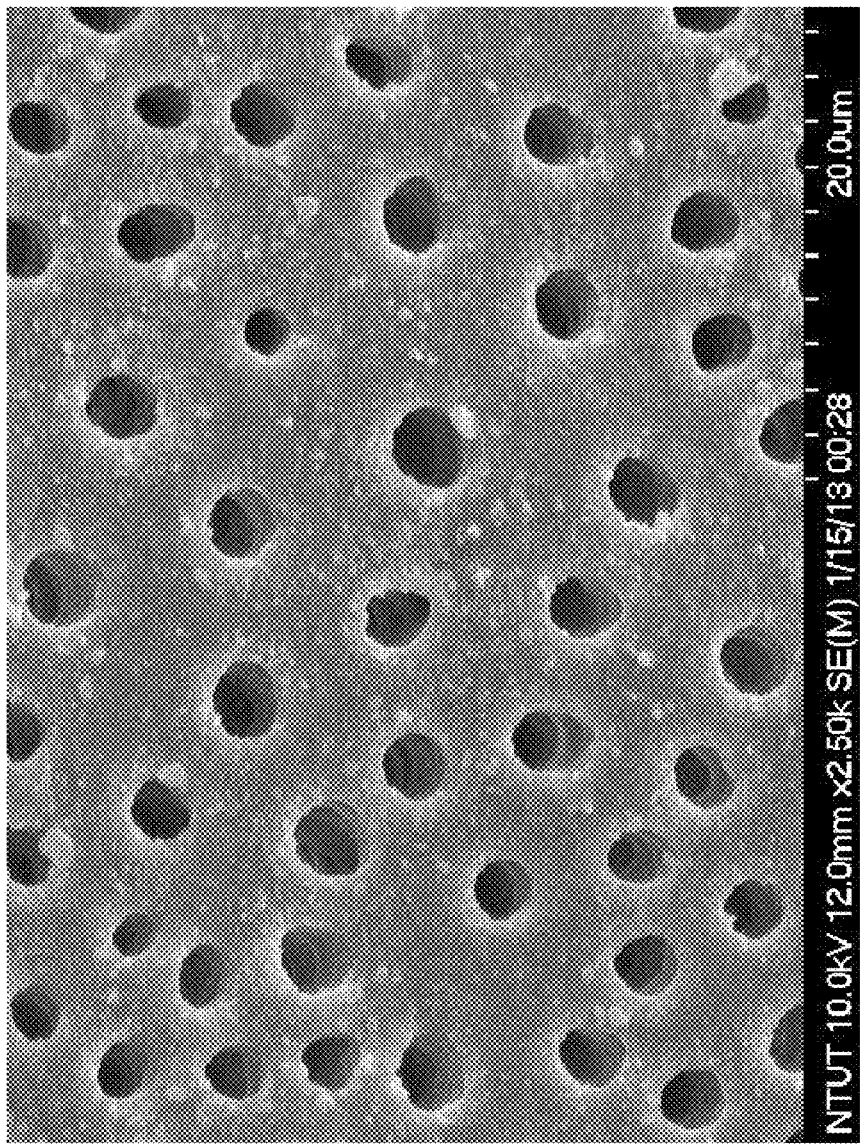
FIG. 2 shows an SEM micrograph taken of a dentin specimen after use of a conventional desensitizing toothpaste.
Figure 3:
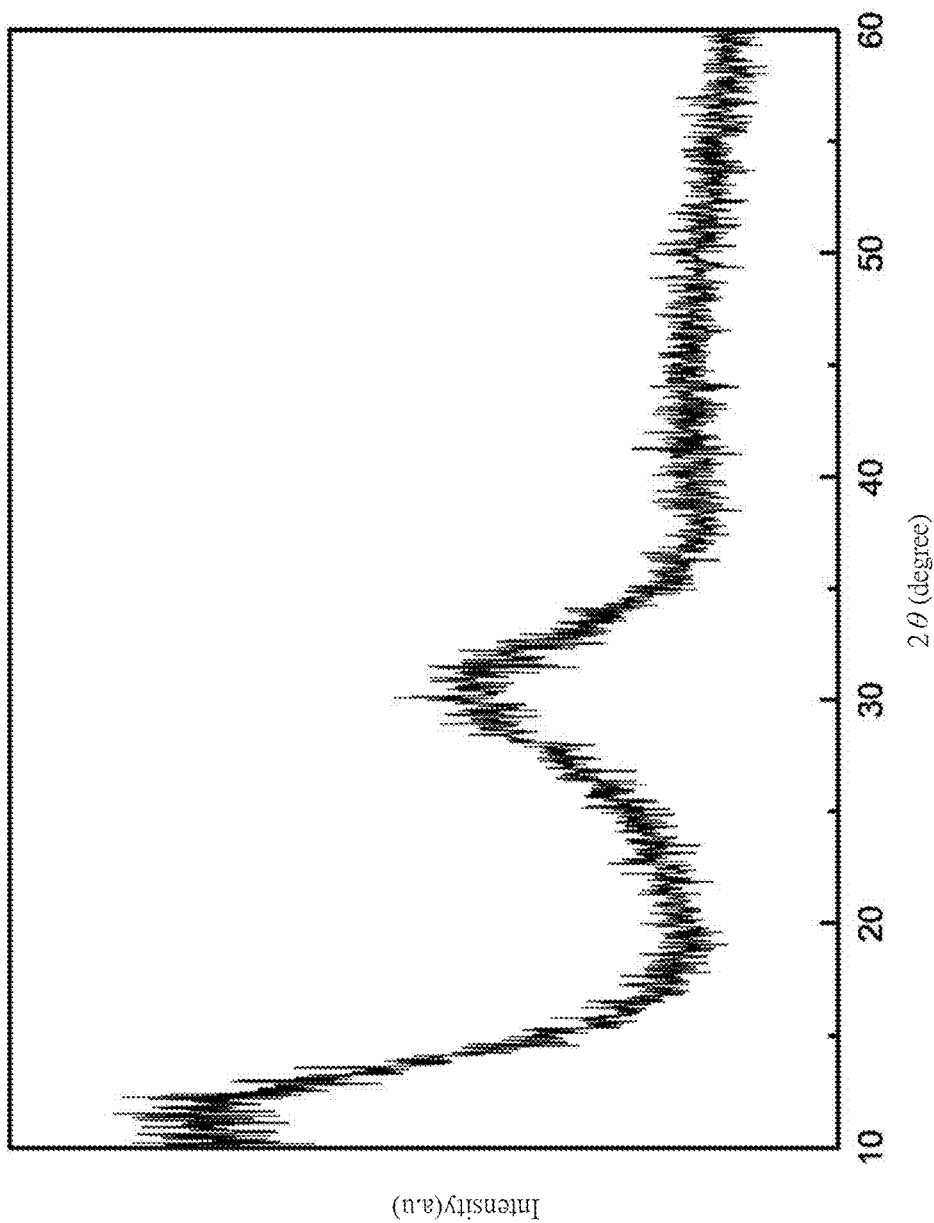
FIG. 3 shows an X-ray diffraction analysis pattern of DP-bioglass according to an embodiment of the present invention.

Referring to FIG. 3, a diffraction angle detection and measurement process is performed on the DP-bioglass thus manufactured with an X-ray diffractometer (Regaku X-ray powder diffractometer, Japan). Crystalline phase is analyzed under the following operation conditions: CuKa (1.5432 Å) X-ray light source and Ni filter; a voltage of 30 kV; a current of 20 mA; a scanning speed of 4°/min; and a scanning angle $2\theta=10\sim60°$. The detected diffraction peak is compared with reference patterns of JCPDS by means of a computer-based automatic pairing system to evaluate the crystalline phase and crystallization of the specimens under test.

Figure 4:
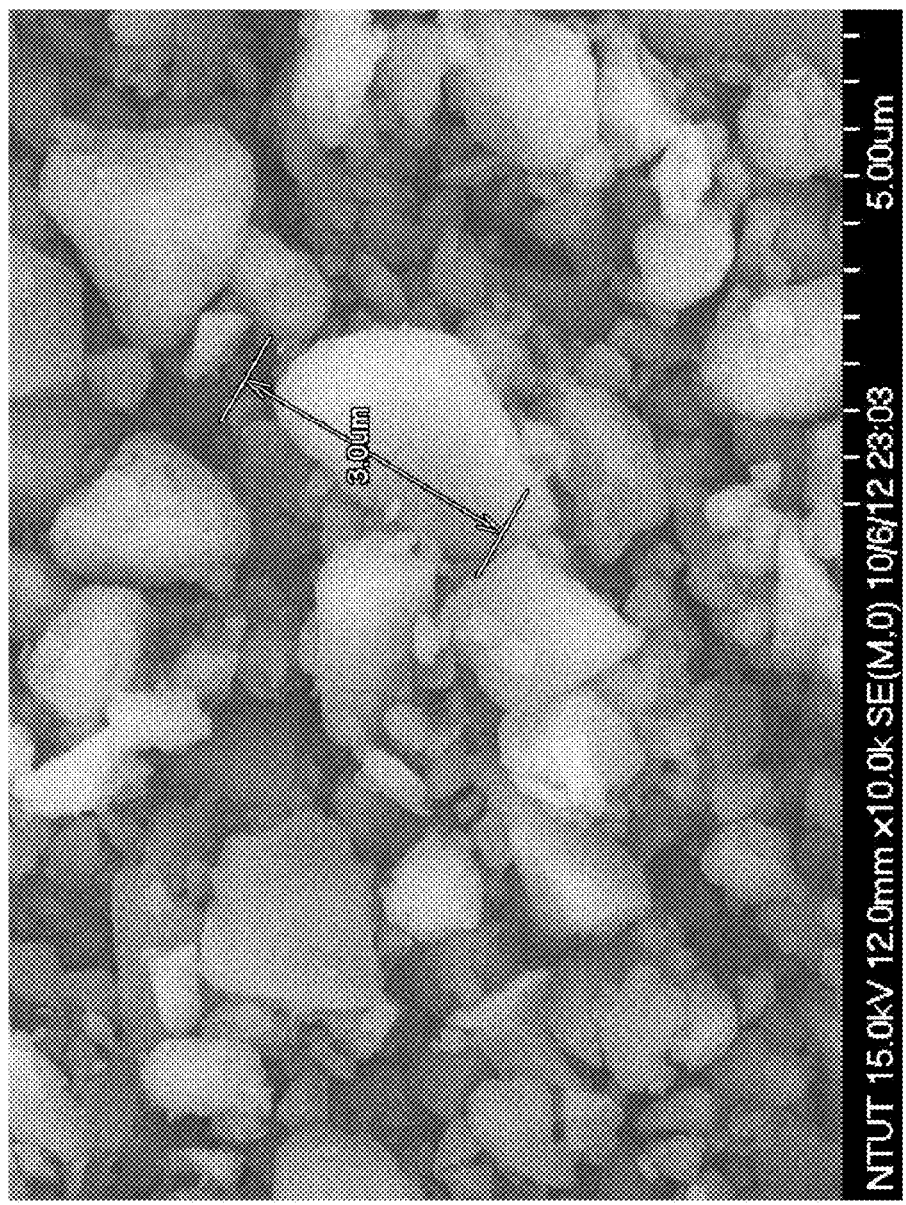
FIG. 4 shows an SEM micrograph taken of DP-bioglass according to an embodiment of the present invention.

Referring to FIG. 4, the DP-bioglass thus manufactured is examined with a field emission scanning electron microscope (Hitachi-S4700) under a high magnification of 10000× to study the patterns and size of the particles of the DP-bioglass powder, and then the patterns of the particles of the DP-bioglass powder are recorded with an image capturing and processing system (analySiS 3.0, Soft Imaging System GmbH, Germany), wherein the size of the particles of the DP-bioglass powder is 3 μm.

The DP-bioglass accounts for 5% to 40%, preferably 15% to 30%, and most preferably 15% to 25% of the total weight of the desensitizing toothpaste. In this regard, the DP-bioglass not only functions as a material for use in occluding the dentinal tubules, but also functions as an abrasive contained in the desensitizing toothpaste. The abrasive scrubs dental plaque, stains, and food residue off the teeth. Hence, the abrasive must have a certain degree of rigidity so that its grinding effect is great enough to bring about a cleaning effect without damaging the tooth surface and periodontal tissue. Furthermore, the desensitizing toothpaste further includes calcium phosphate that functions as the abrasive which accounts for 5% to 25% of the total weight of the desensitizing toothpaste. The desensitizing toothpaste further includes zinc oxide that functions as the abrasive which accounts for 1% to 10% of the total weight of the desensitizing toothpaste.

The thickening agent enables solid ingredients and liquid ingredients of the desensitizing toothpaste to be distributed uniformly therein, by means of diffusion, expansion, and hygroscopy, so as to minimize evaporation of water. The thickening agent affects the viscosity of the desensitizing toothpaste; hence, to allow the desensitizing toothpaste to maintain an appropriate level of viscosity, the thickening agent accounts for 1% to 5%, preferably 1% to 3%, and most preferably 1.5% of the total weight of the desensitizing toothpaste. The thickening agent is made of sodium carboxymethylcellulose.

The purpose of the humectant is to keep the desensitizing toothpaste wet and protect gingiva and dental tissue. The humectant contained in the desensitizing toothpaste accounts for 25% to 35%, and preferably 30%, of the total weight of the desensitizing toothpaste. The humectant is made of glycerol.

The portion of the surfactant that contains hydrophilic radicals and lipophile radicals causes all the ingredients of the desensitizing toothpaste to mix evenly. The surfactant contained in the desensitizing toothpaste accounts for 1% to 5%, preferably 1% to 3%, and most preferably 1.5% of the total weight of the desensitizing toothpaste. The surfactant is made of sodium dodecyl sulfate.

The desensitizing toothpaste further includes potassium nitrate which accounts for 1% to 5% of the total weight of the desensitizing toothpaste. After dissolving in an oral environment, potassium nitrate releases potassium ions. As soon as extracellular potassium ion concentration increases, sodium ion channels open to allow extracellular sodium ions to enter the cell; as a result, membrane potential increases to thereby bring about depolarization, such that action potential is generated, thereby opening potassium ion channels. Since the concentration of extracellular potassium ions remains high, intracellular potassium ions cannot flow outward; as a result, membrane potential cannot restore, and cell membrane cannot polarize any more. In such a situation, even if the cell is subjected to a stimulus, it cannot generate action potential; as a result, nerve conduction is blocked, thereby alleviating dentin hypersensitivity temporarily.

Potassium nitrate provides short-acting anti-hypersensitivity efficacy. As soon as the DP-bioglass is released and recrystallized, the dentinal tubules are closed effectively to thereby achieve long-acting anti-hypersensitivity efficacy. Hence, the desensitizing toothpaste achieves both short-acting and long-acting anti-hypersensitivity efficacy when it contains potassium nitrate.

The desensitizing toothpaste further includes sodium dihydrogen phosphate which accounts for 0.001% to 2% of the total weight of the desensitizing toothpaste. Sodium dihydrogen phosphate provides phosphate ions in an oral environment and thus increases phosphate ion concentration to thereby increase the chance that calcium phosphate precipitates to form hydroxyapatite crystalline. Furthermore, sodium dihydrogen phosphate adjusts and attains the required range of pH value of the desensitizing toothpaste.

The desensitizing toothpaste further includes phosphoric acid which accounts for 0.001% to 2% of the total weight of the desensitizing toothpaste. Phosphoric acid provides an acidic environment and thus speeds up the dissolution of the DP-bioglass. Furthermore, phosphoric acid provides phosphate ions and thus increases phosphate ion concentration, thereby increasing the chance that calcium phosphate precipitates to form hydroxyapatite crystalline. Furthermore, phosphoric acid adjusts and attains the required range of pH value of the desensitizing toothpaste.

The desensitizing toothpaste further includes a fluoride. During tooth brushing, the fluoride-containing desensitizing toothpaste releases fluoride ions into the oral cavity to not only enhance remineralization of teeth but also reduce demineralization of teeth. In Taiwan, related law requires that the concentration of fluoride ions contained in toothpaste be less than 1450 ppm. Hence, to comply with the related law, the fluoride contained in the desensitizing toothpaste of the present invention accounts for 0.1% to 0.2%, and preferably around 0.15%, of the total weight of the desensitizing toothpaste. The fluoride is sodium fluoride.

The desensitizing toothpaste further includes a flavoring agent. The flavoring agent provides various odors while tooth brushing is underway, so as to make the user's breath nicer or enjoy tooth brushing. The flavoring agent accounts for 0.1% to 0.2% of the total weight of the desensitizing toothpaste. The flavoring agent is made of mint and accounts for 0.15% of the total weight of the desensitizing toothpaste.

The desensitizing toothpaste further includes water which accounts for 10% to 25% of the total weight of the desensitizing toothpaste, so as to dissolve or mix the aforesaid ingredients The first illustrative embodiment of the desensitizing toothpaste is described as follows: based on the total weight of the desensitizing toothpaste, provide 16% by weight of calcium phosphate powder, 5% by weight of zinc oxide powder, 20% by weight of the DP-bioglass powder, 1% by weight of sodium dihydrogen phosphate powder, 1.5% by weight of sodium carboxymethylcellulose powder, 1.5% by weight of sodium dodecyl sulfate powder, and 0.15% by weight of sodium fluoride powder, and mix the aforesaid powders. Afterward, provide 30% by weight of glycerol, 1% by weight of phosphoric acid, 0.15% by weight of mint, and 23.7% by weight of water, and mix the aforesaid liquid ingredients. Finally, blend the mixed powders and the mixed liquid ingredients in a large beaker to finalize the manufacturing of the desensitizing toothpaste.

The second illustrative embodiment of the desensitizing toothpaste is described as follows: based on the total weight of the desensitizing toothpaste, provide 17% by weight of calcium phosphate powder, 5% by weight of zinc oxide powder, 20% by weight of the DP-bioglass powder, 1.5% by weight of sodium carboxymethylcellulose powder, 1.5% by weight of sodium dodecyl sulfate powder, and 0.15% by weight of sodium fluoride powder, and mix the aforesaid powders. Afterward, provide 30% by weight of glycerol, 2% by weight of potassium nitrate, 0.15% by weight of mint, and 22.7% by weight of water, and mix the aforesaid liquid ingredients. Finally, blend the mixed powders and the mixed liquid ingredients in a large beaker to finalize the manufacturing of the desensitizing toothpaste.

The third illustrative embodiment of the desensitizing toothpaste is described as follows: based on the total weight of the desensitizing toothpaste, provide 17% by weight of calcium phosphate powder, 5% by weight of zinc oxide powder, 20% by weight of the DP-bioglass powder, 1.5% by weight of sodium carboxymethylcellulose powder, 1.5% by weight of sodium dodecyl sulfate powder, and 0.15% by weight of sodium fluoride powder, and mix the aforesaid powders. Afterward, provide 30% by weight of glycerol, 1% by weight of phosphoric acid, 0.15% by weight of mint, and 23.7% by weight of water, and mix the aforesaid liquid ingredients. Finally, blend the mixed powders and the mixed liquid ingredients in a large beaker to finalize the manufacturing of the desensitizing toothpaste.

The fourth illustrative embodiment of the desensitizing toothpaste is described as follows: based on the total weight of the desensitizing toothpaste, provide 17% by weight of calcium phosphate powder, 5% by weight of zinc oxide powder, 20% by weight of the DP-bioglass powder, 1.5% by weight of sodium carboxymethylcellulose powder, 1.5% by weight of sodium dodecyl sulfate powder, and 0.15% by weight of sodium fluoride powder, and mix the aforesaid powders. Afterward, provide 30% by weight of glycerol, 0.15% by weight of mint, and 24.7% by weight of water, and mix the aforesaid liquid ingredients. Finally, blend the mixed powders and the mixed liquid ingredients in a large beaker to finalize the manufacturing of the desensitizing toothpaste.

The fifth illustrative embodiment of the desensitizing toothpaste is described as follows: based on the total weight of the desensitizing toothpaste, provide 16% by weight of calcium phosphate powder, 5% by weight of zinc oxide powder, 20% by weight of the DP-bioglass powder, 1% by weight of sodium dihydrogen phosphate powder, 1.5% by weight of sodium carboxymethylcellulose powder, 1.5% by weight of sodium dodecyl sulfate powder, and 0.15% by weight of sodium fluoride powder, and mix the aforesaid powders. Afterward, provide 30% by weight of glycerol, 1% by weight of phosphoric acid, 0.15% by weight of mint, 2% by weight of potassium nitrate, and 21.7% by weight of water, and mix the aforesaid liquid ingredients. Finally, blend the mixed powders and the mixed liquid ingredients in a large beaker to finalize the manufacturing of the desensitizing toothpaste.

To prove that the aforesaid desensitizing toothpaste is capable of occluding the dentinal tubules and thereby alleviating dentin hypersensitivity, the embodiment of the present invention further entails: collecting several human molars which have just been extracted, wherein the crowns of the molars are intact and free from caries or fillings; removing scales and periodontal tissues from the surface of the teeth by means of an ultrasonic scaler (Sonicflex 2000, Kavo Co., Biberbach, Germany); removing the enamel on the occlusal surface of the molars in the horizontal direction with a diamond blade (Buehler watering blade, 10.2 cm×0.3 mm, arbor size ½ inch, series15LC diamond, Buehler LTD., MA, USA) of a low speed saw (Isomet low speed saw, Buehler LTD., MA, USA), and then incising the molars along the necks thereof with the diamond blade by a distance of 2 mm and in a parallel direction, so as to obtain dentin specimens for use in experiments; immersing all the dentin specimens in a 17% EDTA solution, and cleaning the dentin specimens in an ultrasonic cleaner for two minutes to remove impurities; taking out the dentin specimens, rinsing them with a large amount of distilled water; and drying the dentin specimens in an oven.

Figure 5A:
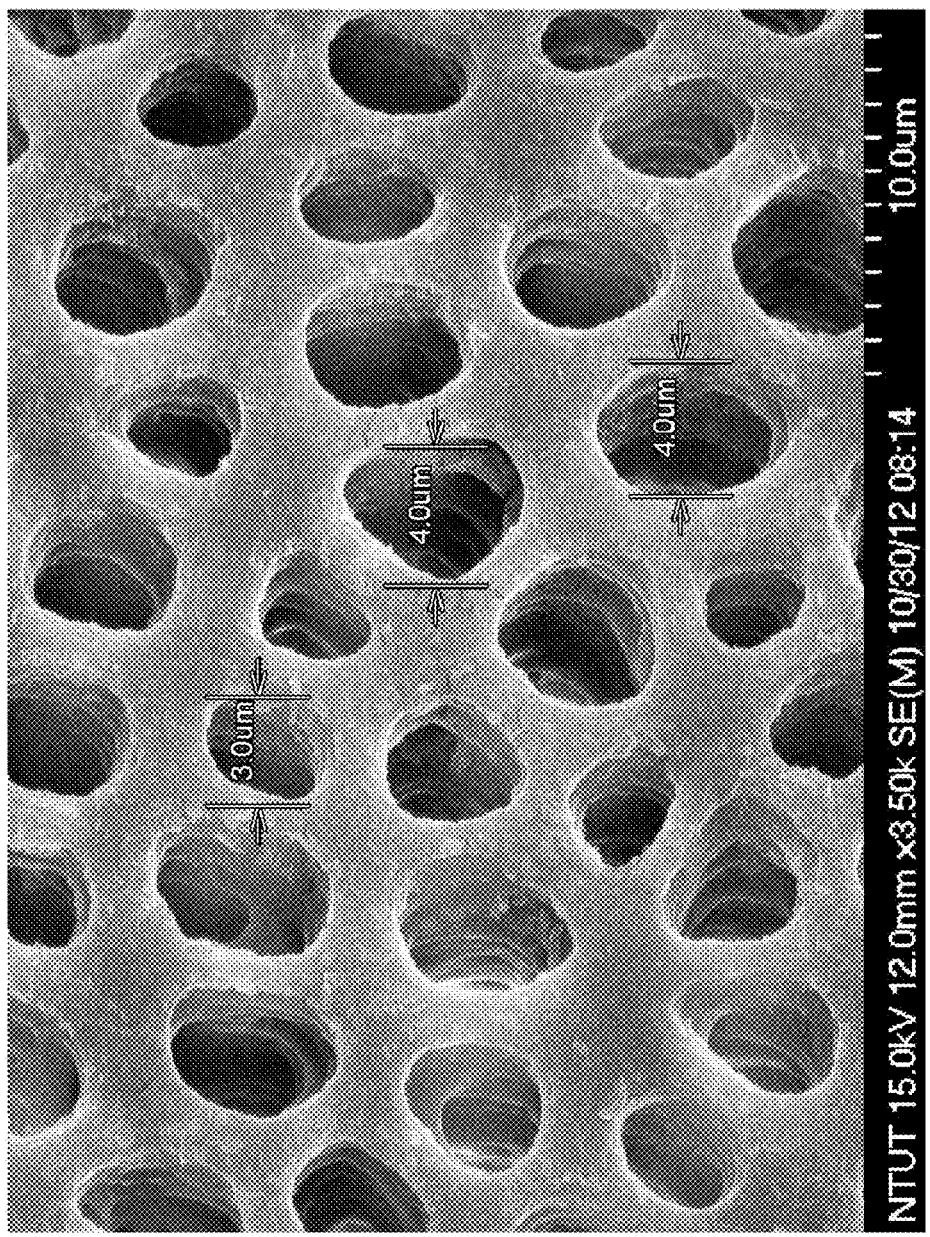
FIG. 5A shows an SEM micrograph taken of the surface of a dentin specimen before use of the desensitizing toothpaste according to an embodiment of the present invention.
Figure 5B:
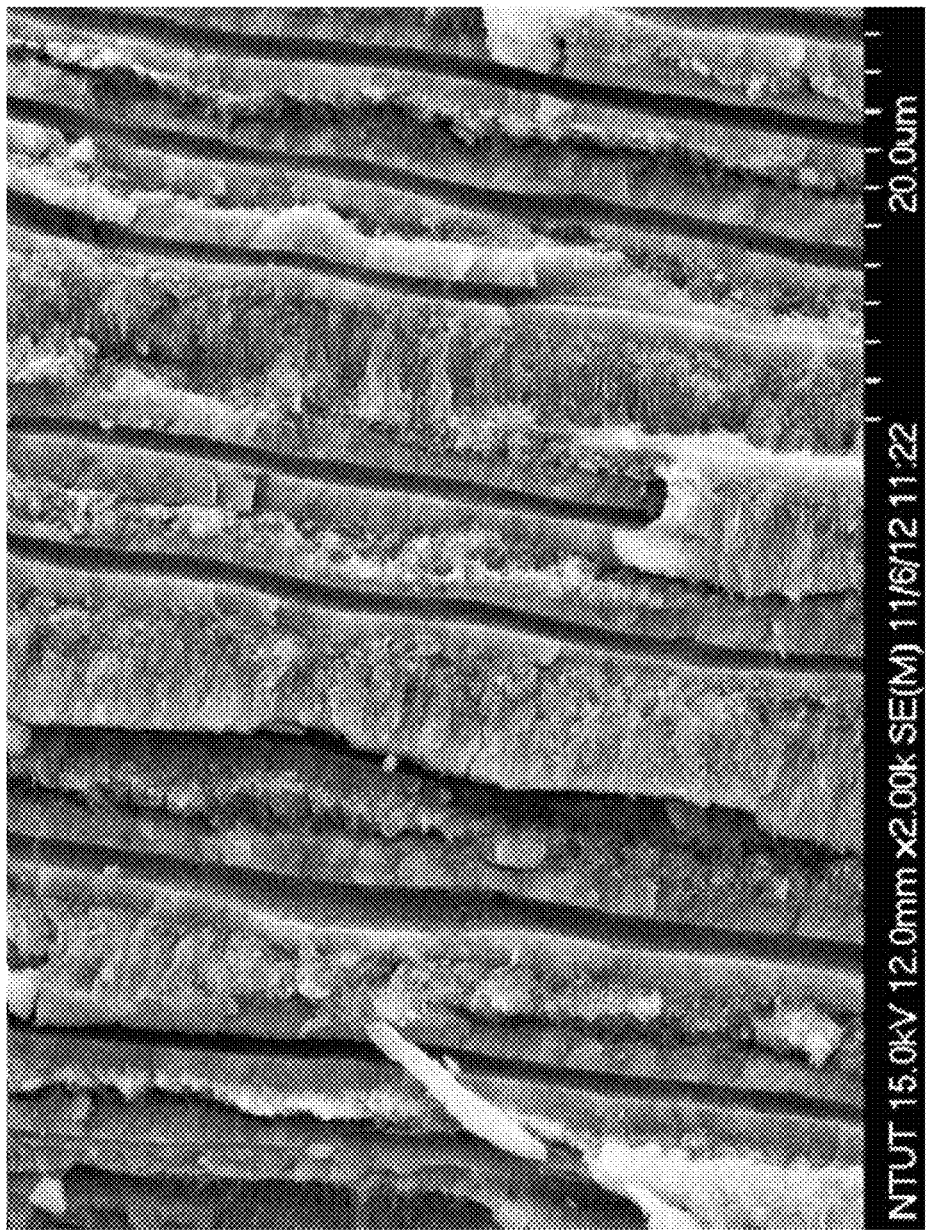
FIG. 5B shows an SEM micrograph taken of the cross-section of a dentin specimen before use of the desensitizing toothpaste according to an embodiment of the present invention.

Referring to FIG. 5A and FIG. 5B, the openings of the dentinal tubules and the cross-sections of the dentinal tubules of the dentin specimens are examined with an electron microscope (Topcon ABT-60, Japan). The examination reveals the following: no crystalline substances are deposited at the openings of the dentinal tubules, nor are the dentinal tubules occluded with crystalline substances; and the openings of the dentinal tubules have a diameter of 3.0 µm to 4.0 µm approximately.

Afterward, the dentin specimens are scrubbed for 10 minutes, using the desensitizing toothpaste of the embodiment of the present invention and artificial saliva. After being scrubbed, particles are rinsed off the surface of the dentin specimens with water. Then, the dentin specimens are dried before being cleaned with an ultrasonic scaler (Sonicflex 2000, Kavo Co., Biberbach, Germany). Afterward, the dentin specimens undergo a dehydration process, using alcohol of sequential concentrations. The dehydration process entails immersing the dentin specimens in 50%, 70%, 80%, 90%, 95% alcohols in sequence, each for 15 minutes, and then immersing the dentin specimens in 100% alcohol twice, each for 15 minutes. After being dried, the dentin specimens are adhered, with carbon adhesive tape, to a platform in order to undergo a coating process with an ionic coater (sputter coater, BIO-RED SC 502, Fisons plc Registered Office, England). Finally, the dentin specimens are examined with an electron microscope (Topcon ABT-60, Japan) for the presence of crystalline substances deposited and occlusion of the openings of the dentinal tubules.

Figure 6A:
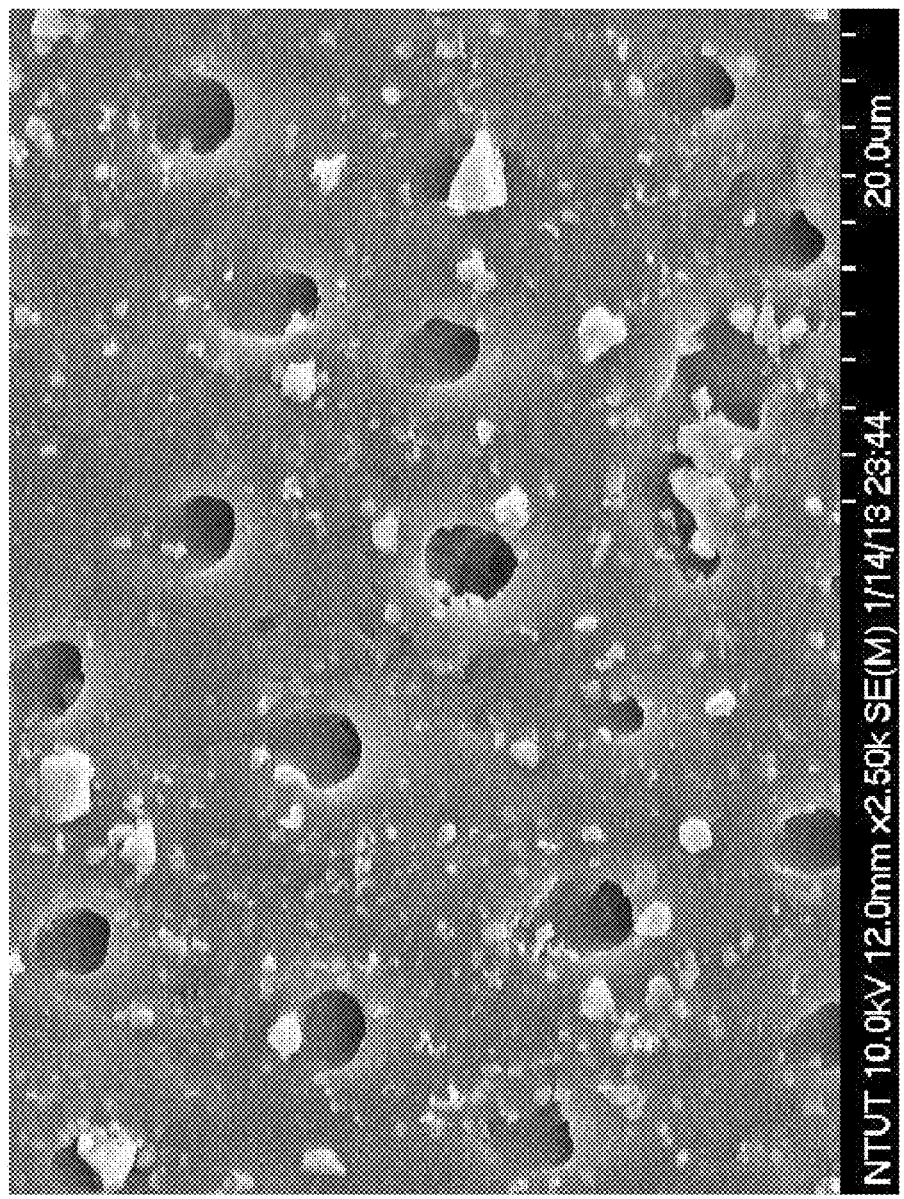
FIG. 6A shows an SEM micrograph taken of the surface of a dentin specimen after use of the desensitizing toothpaste according to an embodiment of the present invention.
Figure 6B:
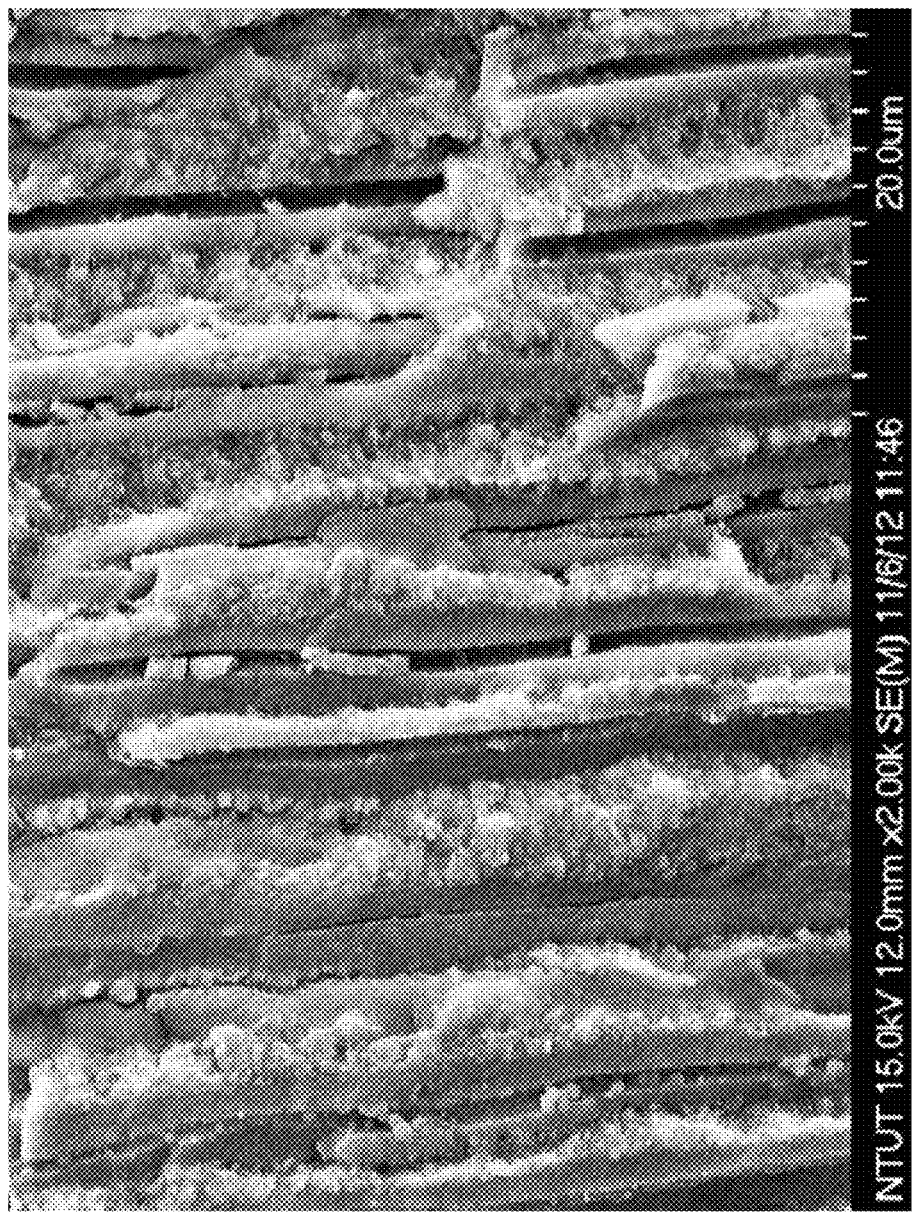
FIG. 6B shows one of SEM micrographs taken of the cross-section of a dentin specimen after use of the desensitizing toothpaste according to an embodiment of the present invention.
Figure 6C:
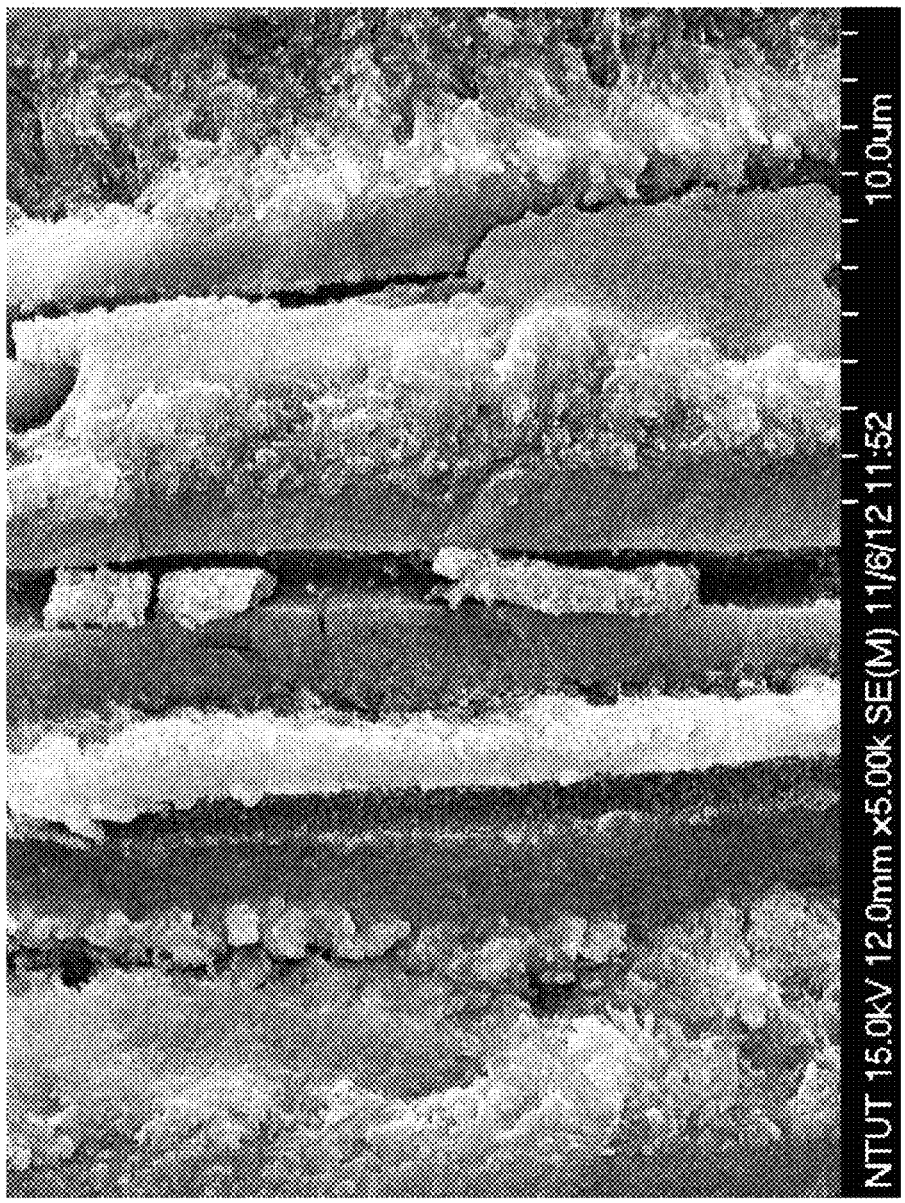
FIG. 6C shows another one of SEM micrographs taken of the cross-section of a dentin specimen after use of the desensitizing toothpaste according to the embodiment of the present invention.
Figure 6D:
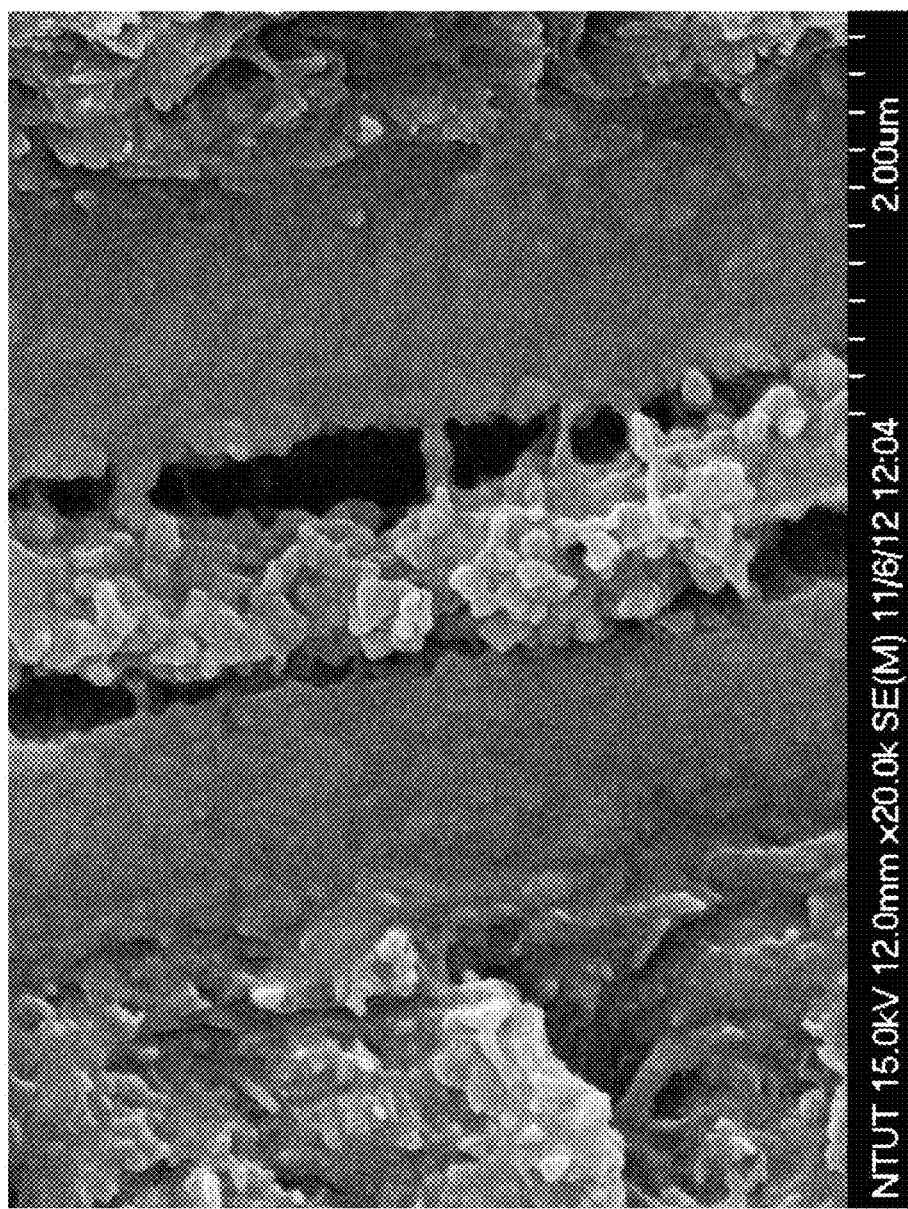
FIG. 6D shows still another one SEM micrographs taken of the cross-section of a dentin specimen after use of the desensitizing toothpaste according to an embodiment of the present invention.

FIG. 6A through FIG. 6D are described hereunder. FIG. 6A shows an electron micrograph taken of the openings of the dentinal tubules in the dentin specimens after use of the desensitizing toothpaste according to the embodiment of the present invention, wherein the dentin specimens are examined under an electron microscope. FIG. 6B through FIG. 6D show electron micrographs taken of the cross-sections of the dentinal tubules, revealing the following: not only are crystalline substances deposited in the vicinity of the openings of the dentinal tubules and inside the dentinal tubules, but the crystalline substances thus deposited also occlude a portion of the dentinal tubules to thereby diminish the openings of the dentinal tubules, thereby alleviating dentin hypersensitivity. Hence, the desensitizing toothpaste of the embodiment of the present invention not only achieves lasting alleviation of dentin hypersensitivity, but also contains potassium nitrate for providing temporary relief, thereby achieving both short-acting and long-acting anti-hypersensitivity efficacy.

The foregoing embodiments are illustrative of the characteristics of the present invention so as to enable a person skilled in the art to understand the contents disclosed herein and implement the present invention accordingly. The embodiments, however, are not intended to restrict the scope of the present invention, which is defined only by the appended claims. Hence, all equivalent modifications and changes which do no depart from the spirit of the present invention should be encompassed by the claims.

What is claimed is:

1. A desensitizing toothpaste, comprising:
   DP-bioglass powder comprising 8.4% of $Na_2O$, 40.6% of CaO, 39% of $SiO_2$, and 12% of $P_2O_5$ based on total weight of the DP-bioglass, wherein the desensitizing toothpaste comprises 5% to 40% by weight of the DP-bioglass powder based on total weight of the desensitizing toothpaste;
   a thickening agent which accounts for 1% to 5% of the total weight of the desensitizing toothpaste;
   a humectant which accounts for 25% to 35% of the total weight of the desensitizing toothpaste;
   a surfactant which accounts for 1% to 5% of the total weight of the desensitizing toothpaste;
   phosphoric acid which accounts for 0.001% to 2% of the total weight of the desensitizing toothpaste; and
   sodium dihydrogen phosphate which accounts for 0.001% to 2% of the total weight of the desensitizing toothpaste,
   wherein the DP-bioglass powder is prepared by a process consisting essentially of the following steps: (a) heating evenly mixed material powder of $Na_2O$, CaO, $SiO_2$, and $P_2O_5$ to obtain molten glass; (b) quenching the molten glass in water to obtain DP-bioglass; and (c) grinding the DP-bioglass.

2. The desensitizing toothpaste of claim 1, further comprising potassium nitrate which accounts for 1% to 5% of the total weight of the desensitizing toothpaste.

3. The desensitizing toothpaste of claim 1, further comprising fluoride which accounts for 0.1% to 0.2% of the total weight of the desensitizing toothpaste.

4. The desensitizing toothpaste of claim 1, further comprising a flavoring agent which accounts for 0.1% to 0.2% of the total weight of the desensitizing toothpaste.

5. The desensitizing toothpaste of claim 1, wherein the phosphoric acid is present at 0.8% to 2% of the total weight of the desensitizing toothpaste so as to promote hydroxyapatite crystalline formation via calcium phosphate precipitation.

* * * * *